United States Patent
Lee (10) Patent No.: US 8,812,115 B2
(45) Date of Patent: Aug. 19, 2014

(54) SYSTEM AND METHOD FOR REDUCING EXCITABILITY OF DORSAL ROOT FIBER BY INTRODUCING STOCHASTIC BACKGROUND NOISE

(75) Inventor: Dongchul Lee, Valencia, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 643 days.

(21) Appl. No.: 12/501,127

(22) Filed: Jul. 10, 2009

(65) Prior Publication Data

US 2011/0009923 A1    Jan. 13, 2011

(51) Int. Cl.
 *A61N 1/00* (2006.01)
 *A61N 1/36* (2006.01)

(52) U.S. Cl.
 CPC .................. *A61N 1/36071* (2013.01)
 USPC ............. 607/46; 607/45; 607/55; 607/56; 607/57; 607/73

(58) Field of Classification Search
 USPC .................... 607/45, 46, 73, 55–57
 See application file for complete search history.

(56) References Cited

U.S. PATENT DOCUMENTS

| | | | |
|---|---|---|---|
| 4,338,945 A * | 7/1982 | Kosugi et al. | 607/46 |
| 5,643,330 A | 7/1997 | Holsheimer et al. | |
| 6,249,704 B1 * | 6/2001 | Maltan et al. | 607/57 |
| 6,516,227 B1 | 2/2003 | Meadows et al. | |
| 6,560,490 B2 | 5/2003 | Grill et al. | |
| 6,675,046 B2 * | 1/2004 | Holsheimer | 607/46 |
| 6,895,280 B2 | 5/2005 | Meadows et al. | |
| 6,944,501 B1 * | 9/2005 | Pless | 607/45 |
| 6,993,384 B2 | 1/2006 | Bradley et al. | |
| 7,539,538 B2 | 5/2009 | Parramon et al. | |
| 7,742,810 B2 * | 6/2010 | Moffitt et al. | 607/2 |
| 2003/0139781 A1 | 7/2003 | Bradley et al. | |
| 2005/0267546 A1 | 12/2005 | Parramon et al. | |

OTHER PUBLICATIONS

Martinez, Lourdes et al., Stochastic Resonance in the Motor System: Effects of Noise on the Monosynaptic Reflex Pathway of the Cat Spinal Cord, J. Neurophysical 97: 4007-4016, 2007. First published Apr. 11, 2007; doi:10.1152/jn.01164-2006.

* cited by examiner

*Primary Examiner* — Michael Kahelin
*Assistant Examiner* — Mallika D Fairchild
(74) *Attorney, Agent, or Firm* — Vista IP Law Group LLP (57) ABSTRACT

A method and neurostimulator for providing therapy to a patient is provided. In one technique, electrical background energy is conveyed to a first tissue region of the patient in accordance with stochastic parameter, thereby modulating the excitability of the first tissue region, and electrical stimulation energy is conveyed to the first tissue region when its excitability is modulated. In one example, the stimulation energy may be conveyed to a second tissue region of the patient, thereby therapeutically stimulating the second tissue region. In this case, the excitability of the first tissue region is decreased, thereby reducing any adverse effect that the conveyed stimulation energy has on the first tissue region. As another example, the conveyed stimulation energy stimulates the first tissue region, in which case, the excitability of the first tissue region may be increased, thereby enhancing the stimulation of the first tissue region by the conveyed stimulation energy.

48 Claims, 7 Drawing Sheets

SYSTEM AND METHOD FOR REDUCING EXCITABILITY OF DORSAL ROOT FIBER BY INTRODUCING STOCHASTIC BACKGROUND NOISE

FIELD OF THE INVENTION

The present invention relates to tissue stimulation systems, and more particularly, to a system and method for stimulating neural fibers.

BACKGROUND OF THE INVENTION

Implantable neurostimulation systems have proven therapeutic in a wide variety of diseases and disorders. For example, Spinal Cord Stimulation (SCS) techniques, which directly stimulate the spinal cord tissue of the patient, have long been accepted as a therapeutic modality for the treatment of chronic pain syndromes, and the application of spinal cord stimulation has begun to expand to additional applications, such as angina pectoralis and incontinence.

An implantable SCS system typically includes one or more electrode carrying stimulation leads, which are implanted at a stimulation site in proximity to the spinal cord tissue of the patient, and a neurostimulator implanted remotely from the stimulation site, but coupled either directly to the stimulation lead(s) or indirectly to the stimulation lead(s) via a lead extension. The neurostimulation system may further comprise a handheld patient programmer to remotely instruct the neurostimulator to generate electrical stimulation pulses in accordance with selected stimulation parameters. The handheld programmer may, itself, be programmed by a technician attending the patient, for example, by using a Clinician's Programmer (CP), which typically includes a general purpose computer, such as a laptop, with a programming software package installed thereon.

Thus, programmed electrical pulses can be delivered from the neurostimulator to the stimulation lead(s) to stimulate or activate a volume of the spinal cord tissue. In particular, electrical stimulation energy conveyed to the electrodes creates an electrical field, which when strong enough, depolarizes (or "stimulates") the neural fibers within the spinal cord beyond a threshold level, thereby inducing the firing of action potentials (APs) that propagate along the neural fibers to provide the desired efficacious therapy to the patient.

For example, in the context of providing pain relief via SCS, it is believed that the antidromic activation (i.e., the APs propagate in a direction opposite to their normal direction, which in the case of the spinal cord, propagate in the caudal direction) of the spinal cord fibers provides the actual pain relief to the patient by reducing/blocking transmission of smaller diameter pain fibers via interneuronal interaction in the dorsal horn of the spinal cord, while the orthodromic activation (i.e., the APs propagate in their normal direction, which in the case of the spinal cord, propagate in the rostral direction) of the spinal cord fibers generate APs that arrive at the thalamus and are relayed to the sensory cortex, thereby creating a pleasant side-effect in the form of a sensation known as paresthesia, which can be characterized as an tingling sensation that replaces the pain signals sensed by the patient.

The combination of electrodes used to deliver electrical pulses to the targeted tissue constitutes an electrode combination, with the electrodes capable of being selectively programmed to act as anodes (positive), cathodes (negative), or left off (zero). In other words, an electrode combination represents the polarity being positive, negative, or zero. Other parameters that may be controlled or varied include electrical pulse parameters, which may define the pulse amplitude, pulse width, pulse rate, pulse shape, and burst rate. Each electrode combination, along with the electrical pulse parameters, can be referred to as a "stimulation parameter set."

Stimulation energy may be delivered to the electrodes during and after the lead placement process in order to verify that the electrodes are stimulating the target neural elements and to formulate the most effective stimulation regimen. The regimen will dictate which of the electrodes are sourcing current pulses (anodes) and which of the electrodes are sinking current pulses (cathodes) at any given time, as well as the magnitude and duration of the current pulses. The stimulation regimen will typically be one that provides stimulation energy to all of the target tissue that must be stimulated in order to provide the therapeutic benefit, yet minimizes the volume of non-target tissue that is stimulated.

While the electrical stimulation of neurons has generally been successful in providing a therapeutic benefit to the patient, there are instances where the target tissue is not directly adjacent to an electrode and, because the electrical field strength decreases exponentially with distance from the electrodes, a relatively strong electrical field must be created to generate APs in the target neural fibers. The electrical field may, however, also result in the generation of APs in the non-target neural fibers, which are larger size than target fibers or closely located to the electrode. The generation of APs in the non-target neural fibers may, in turn, lead to undesirable outcomes (e.g., discomfort or involuntary movements) for the patient. Because the target neural tissue (i.e., the tissue associated with the therapeutic effects) and non-target neural tissue (i.e., the tissue associated with undesirable side effects) are often juxtaposed, therapeutically stimulating neural tissue while preventing side effects may be difficult to achieve.

For example, in the context of SCS, to provide pain relief without inducing involuntary motor movements or otherwise causing discomfort, the neural fibers in the dorsal column (DC neural fibers), which primarily include sensory neural fibers, may be preferentially stimulated over neural fibers in the dorsal roots (DR neural fibers), which, like the DC neural fibers, includes sensory neural fibers. However, stimulation of the DR neural fibers may also create a monosynaptic reflex in the dorsal horn that inadvertently activates the ventral roots (VR neural fibers), which include motor neural fibers leading to corresponding muscles. While DC nerve fibers are the intended targets in conventional SCS, in fact, the DR nerve fibers often are recruited first because of geometric, anatomical, and physiological reasons.

For example, the DR nerve fibers have larger diameters than the largest nearby DC nerve fibers, and thus, have a lower threshold at which they are excited. Other factors that contribute to the lower threshold needed to excite DR nerve fibers are the different orientations of the DC nerve fibers and DR nerve fibers, the curved shape of the DR nerve fibers, and the inhomogeneity and anisotropy of the surrounding medium at the entrance of the DR nerve fibers into the spinal cord. Thus, DR nerve fibers may still generate APs at lower voltages than will nearby DC nerve fibers. As a result, the DC nerve fibers that are desired to be stimulated have a lower probability to be stimulated than do the DR nerve fibers, and thus, the DR nerve fibers are often recruited, thereby potentially creating a monosynaptic reflect in the dorsal horn that leads to discomfort or muscle twitching, ultimately preventing satisfactory pain relief.

For reasons such as these, it is often desirable to modify the threshold at which neural tissue is activated in a manner that maximizes excitation of the target neural tissue, while minimizing excitation of the non-target neural tissue; that is, to increase the DR/DC fiber threshold ratio. This can be accomplished by medial-laterally aligning an electrode array (i.e., the electrodes are arranged transversely to the neural fibers of the spinal cord), and controlling the shape of the electric field generating activation region of the spinal cord in order to prevent the generation of APs in non-target neural fibers. In particular, an electrical pulse is sunk to a cathodic electrode located at the center of the spinal cord to depolarize the target tissue adjacent the cathodic electrode, thereby creating APs along the DC nerve fibers, while an electrical pulse is sourced to anodic electrodes on both sides of the cathodic electrode to hyperpolarize non-target tissue adjacent the anodic electrodes, thereby increasing the threshold of the DR nerve fibers.

While the stimulation of the spinal cord using a medial-lateral arranged electrode array in this manner has been shown to provide effective pain treatment, this approach does require multiple contacts in the medial-lateral direction, which, given a fixed number of electrodes, decreases the rostro-caudal span of the electrode array along the spinal cord. Furthermore, due to current shunting resulting from the close spacing between anodes required to achieve the selective stimulation field, high stimulation energy thresholds are typically required for medial-lateral electrode arrangements.

There, thus, remains to alternative means for increasing the DR/DC fiber threshold ratio.

SUMMARY OF THE INVENTION

In accordance with a first aspect of the present inventions, a method of providing therapy (e.g., pain relief) to a patient is provided. The method comprises conveying electrical background energy in accordance with at least one stochastic parameter to a first tissue region (e.g. of the patient), thereby modulating the excitability of the first tissue region, and conveying electrical stimulation energy to the first tissue region when its excitability is modulated. The electrical background energy may comprise pulses, in which case, the stochastic parameter(s) may comprise at least one of an interpulse interval, pulse amplitude, pulse shape, and pulse duration. The electrical energy may comprise white noise, in which case, the stochastic parameter(s) may comprise a frequency.

To provide a substantial effect on the excitability of the first tissue region, the electrical background energy may, e.g., be equal to or greater than one-tenth the perception threshold of the patient. The electrical background energy may be subthreshold so as to not, alone, have an effect on the patient, or may be supra-threshold so as to, alone, have a therapeutic effect on the patient. Preferably, the magnitude of the electrical background energy is great enough to have a substantial impact to the therapy of the patient. For example, the magnitude of the electrical background energy may be greater than 2% of the magnitude of the electrical stimulation energy, and in some cases, may be greater than 10% of the magnitude of the electrical stimulation energy. Preferably, the magnitude of the electrical background energy is less than the magnitude of the electrical stimulation energy. For example, the magnitude of the electrical background energy may be less than 50% of the magnitude of the electrical stimulation energy. In any event, the magnitude of the electrical background energy may be adjusted relative to the magnitude of the electrical stimulation energy in order to fine tune the therapeutic effect of the stimulation on the patient.

The electrical background energy may be conveyed during the conveyance of the electrical stimulation energy. For example, the electrical stimulation energy may comprise a train of stimulus pulses having a fixed pulse frequency, and the electrical background energy may be continuous throughout the train of stimulus pulses. The electrical background energy may not be conveyed during the conveyance of the electrical stimulation energy. For example, the electrical stimulation energy may comprise a train of stimulus pulses, and the electrical background energy may take the form of pre-pulses relative to the stimulus pulses.

In one exemplary method, the electrical stimulation energy is further conveyed to a second tissue region of the patient, thereby therapeutically stimulating the second tissue region. In this case, the excitability of the first tissue region is modulated by decreasing the excitability of the first tissue region, thereby reducing any adverse effect that the conveyed electrical stimulation energy has on the first tissue region. For example, the decreased excitability of the first tissue region may prevent stimulation of the first tissue region by the conveyed electrical stimulation energy. The first and second tissue regions may respectively be, e.g., dorsal root (DR) nerve fibers and dorsal column (DC) nerve fibers. In another exemplary method, the conveyed electrical stimulation energy stimulates the first tissue region, and the excitability of the first tissue region is modulated by increasing the excitability of the first tissue region, thereby enhancing the stimulation of the tissue region by the conveyed electrical stimulation energy.

In accordance with a second aspect of the present inventions, a neurostimulator is provided. The neurostimulator comprises a plurality of electrical terminals configured for being electrically coupled to at least one electrode carrying stimulation lead, analog output circuitry configured for generating electrical stimulation energy and for generating electrical background energy having a stochastic frequency, and control circuitry configured for controlling the analog output circuitry to convey the electrical stimulation energy and the electrical background energy to the plurality of electrical terminals.

The characteristics of the electrical stimulation energy and electrical background energy may be the same as the characteristics described above. The analog output circuitry may comprise a white noise generator configured for generating white noise used to generate the electrical background energy. In this case, the analog output circuitry may further comprise a bandpass filter configured for filtering the white noise. If the background energy is pulsed, the analog output circuitry may further comprise a pulse mixer configured for stochastically varying at least one parameter in accordance with the filtered white noise, and outputting the stochastically varied parameter(s) as the stochastic parameter(s) in accordance with which the electrical background energy is generated.

In one embodiment, at least one of the electrical terminals to which the electrical background energy is the same as at least one of the electrical terminals to which the electrical stimulation energy is conveyed. In another embodiment, none of the electrical terminals to which the electrical background energy is conveyed is the same as an electrical terminal to which the electrical stimulation energy is conveyed. The neurostimulator may comprise a case containing the plurality of electrical terminals, analog output circuitry, and control circuitry to form an implantable neurostimulator.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to a spinal cord stimulation (SCS) system. However, it is to be understood that while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
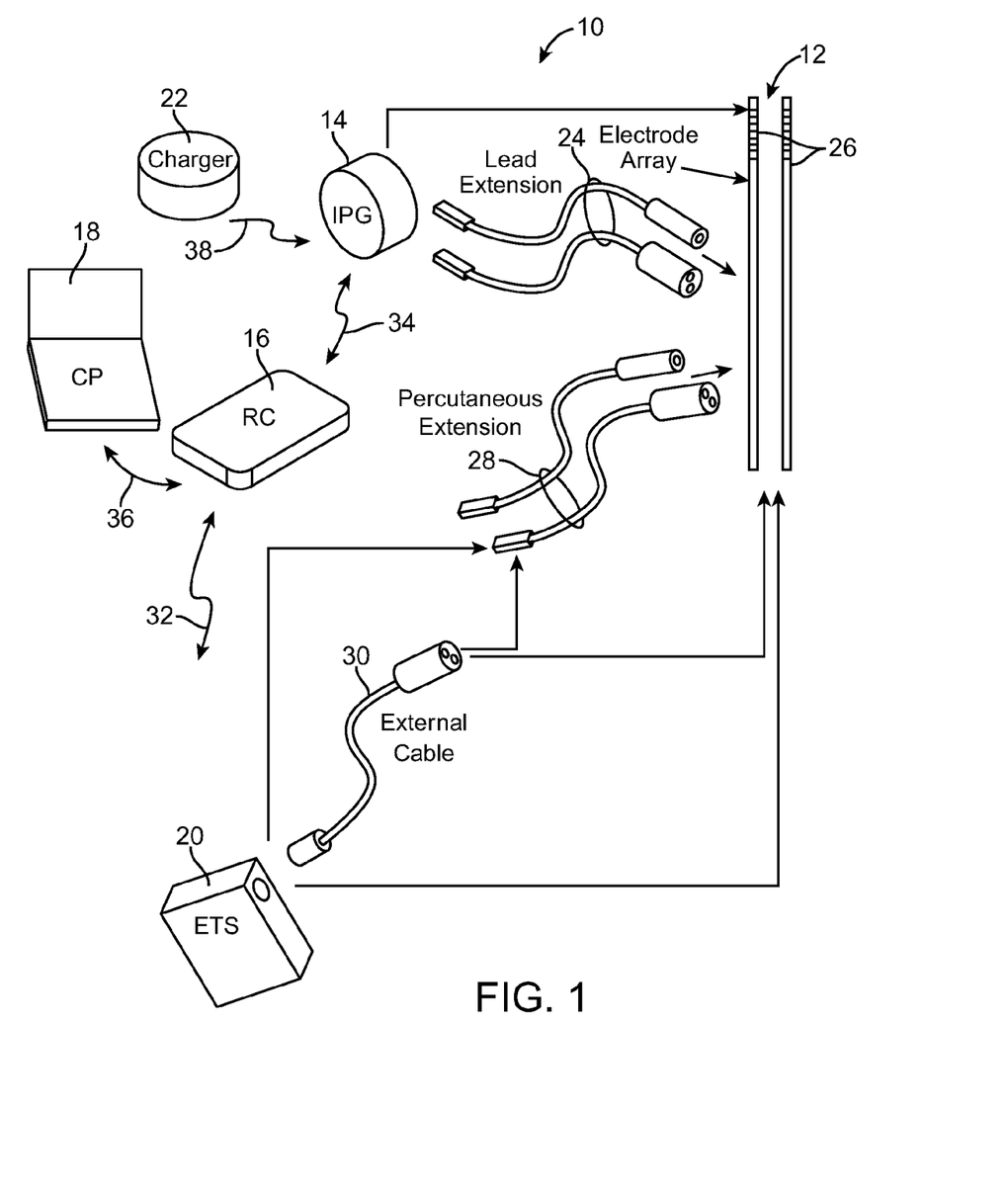
FIG. 1 is plan view of one embodiment of a spinal cord stimulation (SCS) system arranged in accordance with the present inventions.

Turning first to FIG. 1, an exemplary spinal cord stimulation (SCS) system 10 generally includes one or more (in this case, two) implantable stimulation leads 12, a pulse generating device in the form of an implantable pulse generator (IPG) 14, an external control device in the form of a remote controller RC 16, a clinician's programmer (CP) 18, an external trial stimulator (ETS) 20, and an external charger 22.

The IPG 14 is physically connected via one or more percutaneous lead extensions 24 to the stimulation leads 12, which carry a plurality of electrodes 26 arranged in an array. In the illustrated embodiment, the stimulation leads 12 are percutaneous leads, and to this end, the electrodes 26 are arranged in-line along the stimulation leads 12. In alternative embodiments, the electrodes 26 may be arranged in a two-dimensional pattern on a single paddle lead. As will be described in further detail below, the IPG 14 includes pulse generation circuitry that delivers electrical stimulation energy in the form of a pulsed electrical waveform (i.e., a temporal series of electrical pulses) to the electrode array 26 and electrical background energy in accordance with a set of stimulation parameters.

The ETS 20 may also be physically connected via the percutaneous lead extensions 28 and external cable 30 to the stimulation leads 12. The ETS 20, which has similar pulse generation circuitry as that of the IPG 14, also delivers electrical stimulation energy and electrical background energy to the electrode array 26 in accordance with a set of stimulation parameters. The major difference between the ETS 20 and the IPG 14 is that the ETS 20 is a non-implantable device that is used on a trial basis after the stimulation leads 12 have been implanted and prior to implantation of the IPG 14, to test the responsiveness of the stimulation that is to be provided. Further details of an exemplary ETS are described in U.S. Pat. No. 6,895,280, which is expressly incorporated herein by reference.

The RC 16 may be used to telemetrically control the ETS 20 via a bi-directional RF communications link 32. Once the IPG 14 and stimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14.

The CP 18 provides clinician detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18). The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present.

For purposes of brevity, the details of the RC 16, CP 18, ETS 20, and external charger 22 will not be described herein. Details of exemplary embodiments of these devices are disclosed in U.S. Pat. No. 6,895,280, which is expressly incorporated herein by reference.

Figure 2:
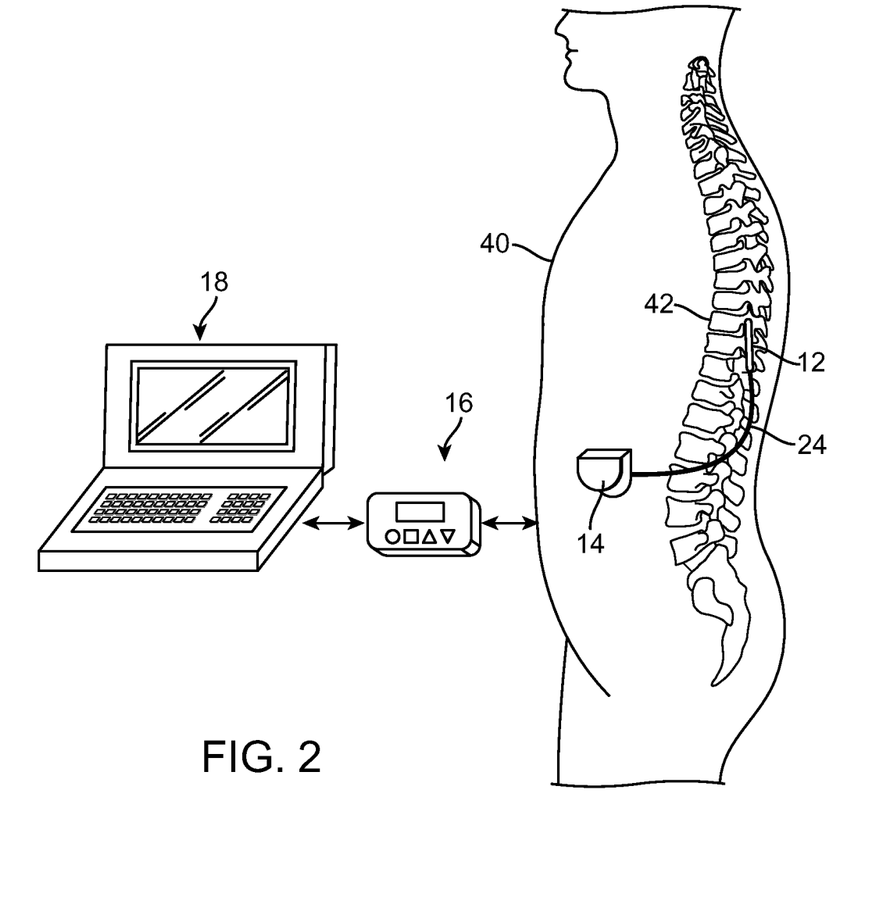
FIG. 2 is a plan view of the SCS system of FIG. 1 in use with a patient.

As shown in FIG. 2, the electrode leads 12 are implanted within the spinal column 42 of a patient 40. The preferred placement of the electrode leads 12 is adjacent, i.e., resting near, or upon the dura, adjacent to the spinal cord area to be stimulated. Due to the lack of space near the location where the electrode leads 12 exit the spinal column 42, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the electrode leads 12. As there shown, the CP 18 communicates with the IPG 14 via the RC 16.

Figure 3:
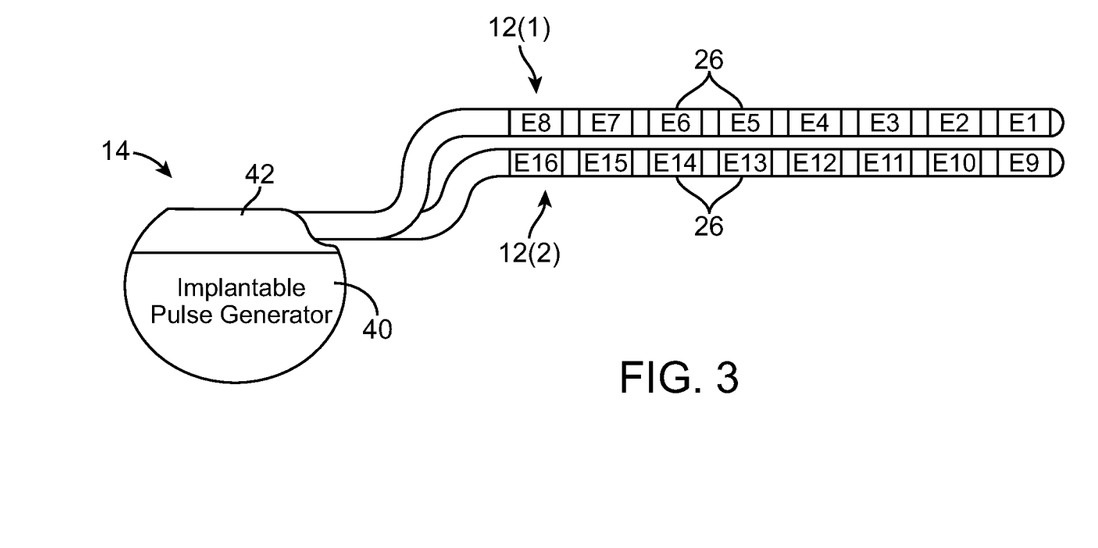
FIG. 3 is a plan view of an implantable pulse generator (IPG) and one embodiment of a stimulation lead used in the SCS system of FIG. 1.

Referring now to FIG. 3, the external features of the stimulation leads 12 and the IPG 14 will be briefly described. One of the stimulation leads 12 has eight electrodes 26 (labeled E1-E8), and the other stimulation lead 12 has eight electrodes 26 (labeled E9-E16). The actual number and shape of leads and electrodes will, of course, vary according to the intended application. The IPG 14 comprises an outer case 50 for housing the electronic and other components (described in further detail below), and a connector 52 to which the proximal ends of the stimulation leads 12 mate in a manner that electrically couples the electrodes 26 to the internal electronics (described in further detail below) within the outer case 50. The outer case 50 is composed of an electrically conductive, biocompatible material, such as titanium, and forms a hermetically sealed compartment wherein the internal electronics are protected from the body tissue and fluids. In some cases, the outer case 50 may serve as an electrode.

As briefly discussed above, the IPG 14 includes battery and pulse generation circuitry that delivers the electrical stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), and pulse rate (measured in pulses per second), pulse shape, and burst rate (measured as the stimulation on duration per unit time).

Electrical stimulation will occur between two (or more) activated electrodes, one of which may be the IPG case 50. Simulation energy may be transmitted to the tissue in a monopolar or multipolar (e.g., bipolar, tripolar, etc.) fashion. Monopolar stimulation occurs when a selected one of the lead electrodes 26 is activated along with the case 50 of the IPG 14, so that stimulation energy is transmitted between the selected electrode 26 and case 50. Bipolar stimulation occurs when two of the lead electrodes 26 are activated as anode and cathode, so that stimulation energy is transmitted between the selected electrodes 26. For example, electrode E3 on the first lead 12 may be activated as an anode at the same time that electrode E11 on the second lead 12 is activated as a cathode. Tripolar stimulation occurs when three of the lead electrodes 26 are activated, two as anodes and the remaining one as a cathode, or two as cathodes and the remaining one as an anode. For example, electrodes E4 and E5 on the first lead 12 may be activated as anodes at the same time that electrode E12 on the second lead 12 is activated as a cathode.

The stimulation energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) stimulation pulse and an anodic (positive) recharge pulse that is generated after the stimulation pulse to prevent direct current charge transfer through the tissue, thereby avoiding electrode degradation and cell trauma. That is, charge is conveyed through the electrode-tissue interface via current at an electrode during a stimulation period (the length of the stimulation pulse), and then pulled back off the electrode-tissue interface via an oppositely polarized current at the same electrode during a recharge period (the length of the recharge pulse).

Significantly, the IPG 14 also comprises circuitry configured for generating electrical background energy having stochastic parameters, which can be associated with a train of stimulus pulses (e.g., squared, sinusoidal, ramped, exponential or triangular shapes) with deterministic parameters in order to advantageously modulate the excitability of neural fibers in a substantial manner. Notably, a stochastic process, which is the counterpart to a deterministic process, is a process where there is some indeterminacy in its future evolution described by probability distributions. This means that even if the initial condition (or starting point) is known, there are many possibilities the process might yield. For example, the frequency or interpulse intervals of the background energy may be varied pseudo-randomly (i.e., a process that appears random, but is not, and exhibits statistical randomness while being generated by an entirely deterministic causal process) or randomly. For the purposes of this specification, the excitability of neural fibers is substantially modified if the modulated excitability has a patient-perceived effect compared to the unmodulated excitability.

Figure 4:
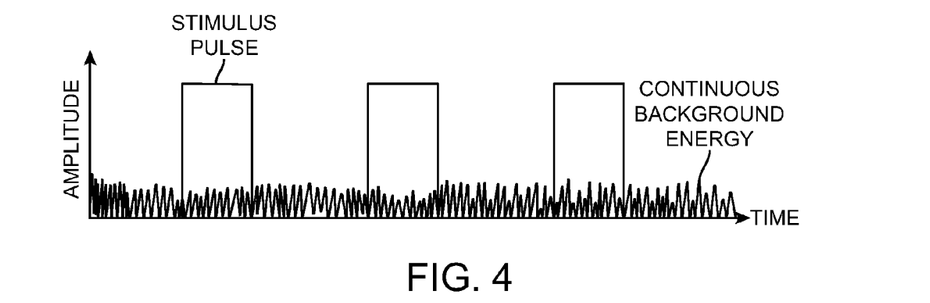
FIG. 4 is a timing diagram of a first set of waveforms for electrical stimulation energy and background energy generated by the IPG of FIG. 3.
Figure 5:
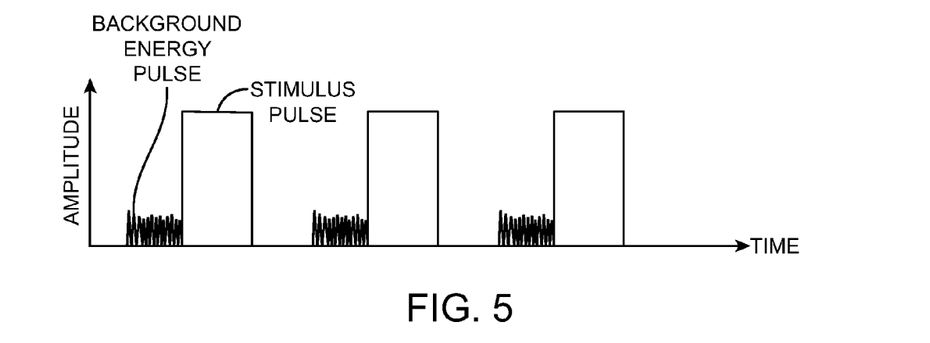
FIG. 5 is a timing diagram of a first set of waveforms for electrical stimulation energy and background energy generated by the IPG of FIG. 3.
Figure 6:
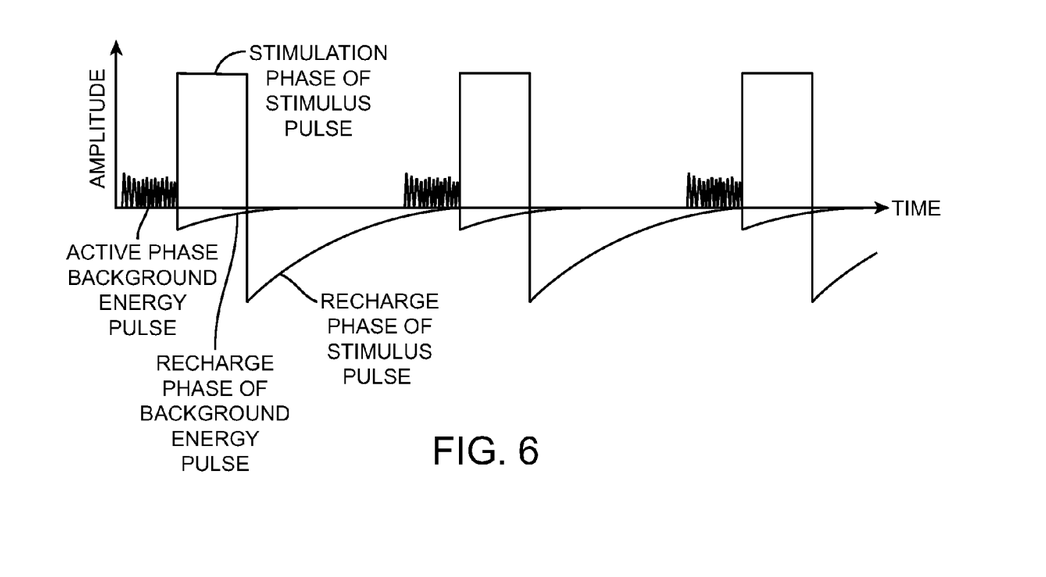
FIG. 6 is a timing diagram of a first set of waveforms for electrical stimulation energy and background energy generated by the IPG of FIG. 3.

As one example, the electrical background energy can be continuously conveyed by the IPG 14 during the conveyance of a train of stimulus pulses, as shown in FIG. 4. Alternatively, rather than conveying the electrical background energy in a continuous manner, the background electrical energy may be pulsed on and off between the stimulus pulses, as illustrated in FIG. 5. As there shown, the background electrical energy takes the form of pre-pulses that are conveyed immediately before the conveyance of the respective pulses in order to condition the tissue prior to delivery of the stimulation energy thereto. Although the stimulus pulses illustrated in FIG. 5 are shown as being monophasic in nature, each of the stimulus pulses may have an active phase and a recharge phase, as illustrated in FIG. 6. As there shown, the background energy also has an active phase and a recharge phase. Although the stimulation energy and background energy are illustrated in FIGS. 4-6 as being anodic, it should be noted that the stimulation energy and background energy can be cathodic.

The frequency spectrum of the electrical background energy may be, e.g., in the range of 100 Hz-20 KHz, preferably in the range of 200 Hz-5 KHz. Preferably, the center of the frequency spectrum of the electrical background energy is greater than the pulse rate of the electrical stimulation energy. For example, the center frequency of the electrical background energy may be five times greater than the pulse rate of the electrical stimulation energy. The magnitude of the electrical background energy is preferably less than the magnitude of the electrical stimulation energy, but greater than a value needed to have a substantial effect on the excitability of the relevant neural fibers. For example, the magnitude of the electrical background energy may be greater than 2%, and more particularly greater than 10%, of the magnitude of the electrical stimulation energy. The magnitude of the electrical background energy may be less than 50% of the magnitude of the electrical stimulation energy.

The magnitude of the electrical background energy may be adjusted relative to the magnitude of the electrical stimulation energy. As will be described in further detail below, the conveyance of electrical background energy to adjacent nerve tissue at a relatively low magnitude will tend to render the nerve tissue more excitable, whereas the conveyance of electrical background energy to adjacent nerve tissue at a relatively high magnitude will tend to render the nerve tissue less excitable. Whether the nerve tissue is selected to be more excitable or less excitable will depend on the particular application.

Figure 7:
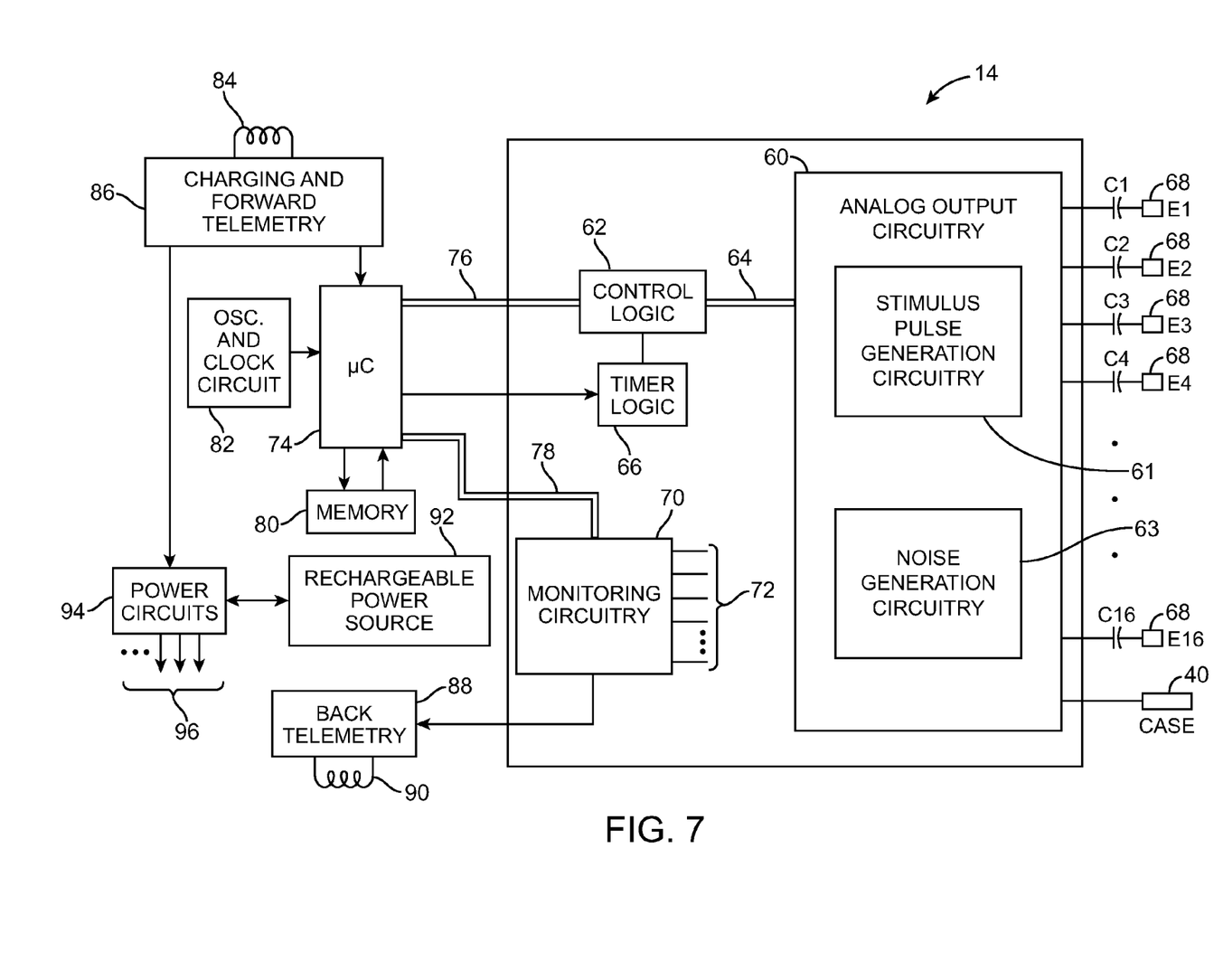
FIG. 7 is a block diagram of the internal components of the IPG of FIG. 3.

Turning next to FIG. 7, the main internal components of the IPG 14 will now be described. The IPG 14 includes analog output circuitry 60 configured for generating both electrical stimulation energy and electrical background energy, each in accordance with a defined pulsed waveform having a specified pulse amplitude, pulse rate, pulse width, pulse shape, and burst rate under control of control logic 62 over data bus 64. The stochastic electrical energy can be generated using bandpass filtered white noise. For the purposes of this specification, "white noise" is a random signal with a substantially flat power spectral density. That is, the signal contains substantially equal power within a fixed bandwidth at any center frequency. The center frequency and band-width of the filter will determine the degree of randomness in the signal. The randomness can be applied to stimulation amplitude, inter-pulse interval, individual pulse shape and pulse width of the background energy. Control of the pulse rate and pulse width of the electrical waveform is facilitated by timer logic circuitry 66, which may have a suitable resolution, e.g., 10 µs. The electrical stimulation energy and electrical background energy generated by the output analog circuitry 60 is output via capacitors C1-C16 to electrical terminals 68 corresponding to the electrodes 26.

The analog output circuitry 60 comprises stimulus pulse generation circuitry 61 for generating the electrical stimulation energy and electrical noise generation circuitry 63 for generating the electrical background energy. The stimulus pulse generation circuitry 61 may either comprise independently controlled current sources for providing electrical stimulation energy of a specified and known amperage to or from the electrical terminals 68, or independently controlled voltage sources for providing electrical stimulation energy of a specified and known voltage at the electrical terminals 68 or to multiplexed current or voltage sources that are then connected to the electrical terminals 68. The operation of the stimulus pulse generation circuitry 61, including alternative embodiments of suitable output circuitry for performing the same function of generating stimulation pulses of a prescribed amplitude and width, is described more fully in U.S. Pat. Nos. 6,516,227 and 6,993,384, which are expressly incorporated herein by reference.

The electrical noise generation circuitry 63 may be coupled between a fixed number of terminals 68, one of which may be the case, or may be selectively coupled between any number of terminals 68, e.g., via a switch (not shown). Depending on the desired effect, the electrical background energy may be conveyed to at least one electrical terminal 68 to which the electrical stimulation energy is conveyed, or the electrical background energy may be conveyed to none of the electrical terminals 68 to which the electrical stimulation energy is conveyed, as will be described in further detail below. It follows from this that the electrical stimulation energy may be delivered in a bipolar manner, whereas the electrical background energy may be delivered in a monopolar manner.

Figure 8:
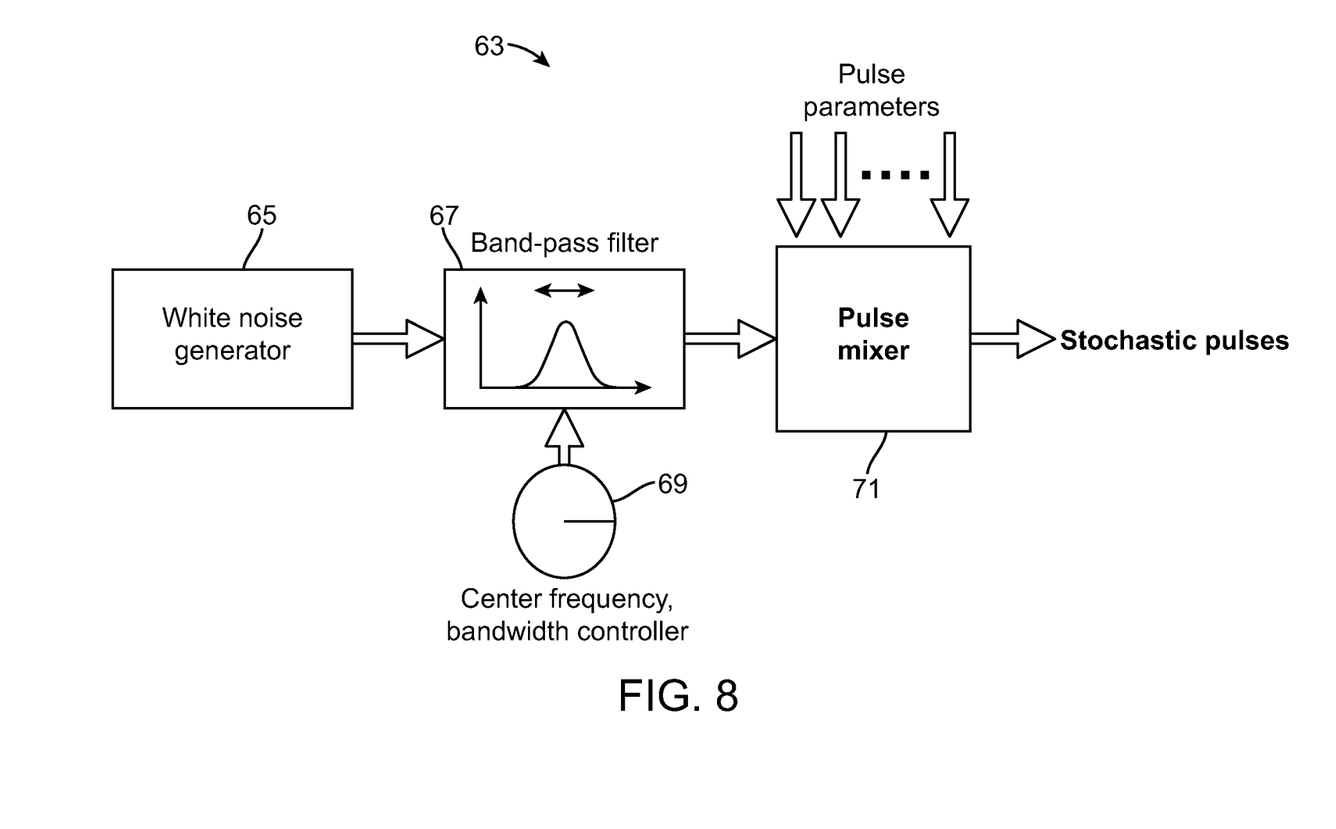
FIG. 8 is a block diagram of noise generation circuitry used in the IPG of FIG. 7.

Referring to FIG. 8, one embodiment of the noise generation circuitry 63 comprises a white noise generator 65 configured for generating white noise used to generate the electrical background energy. The noise generation circuitry 63 further comprises a bandpass filter 67 configured for filtering the white noise output by the white noise generator 65. The bandpass filter 67 includes a tuner 69 configured for adjusting the center frequency and bandwidth of the bandpass. In this manner, the tuner 69 can be used (e.g., by transmitting a control signal from an external control device, such as the RC 16 or IPG 18) to tune the electrical background energy to provide the optimal therapy for the patient. The noise generation circuitry 63 further comprises a pulse mixer 71 configured for stochastically varying one or more pulse parameters (e.g., pulse rate, pulse amplitude, and/or pulse duration) based on the filtered white noise output by the bandpass filter 67, and generating and outputting the pulsed background pulses in accordance with the varied pulse parameter(s). Alternatively, instead of directly generating the stochastic energy, circuitry can be used to stochastically vary the parameter(s) based on the filtered white noise. These stochastic parameter(s) can be then be used by the microcontroller (described below). Alternatively, the noise generation circuitry 63 does not use a bandpass filter and pulse mixer, in which case, the noise generation circuitry 63 may directly output the filtered white noise to the electrodes.

Referring back to FIG. 7, the IPG 14 further comprises monitoring circuitry 70 for monitoring the status of various nodes or other points 72 throughout the IPG 14, e.g., power supply voltages, temperature, battery voltage, and the like. The monitoring circuitry 70 is also configured for measuring electrical parameter data (e.g., electrode impedance and/or electrode field potential). The IPG 14 further comprises processing circuitry in the form of a microcontroller (µC) 74 that controls the control logic 62 over data bus 76, and obtains status data from the monitoring circuitry 70 via data bus 78. The IPG 14 further comprises memory 80 and oscillator and clock circuit 82 coupled to the microcontroller 74. The microcontroller 74, in combination with the memory 80 and oscillator and clock circuit 82, thus comprise a microprocessor system that carries out a program function in accordance with a suitable program stored in the memory 80. Alternatively, for some applications, the function provided by the microprocessor system may be carried out by a suitable state machine.

Thus, the microcontroller 74 generates the necessary control and status signals, which allow the microcontroller 74 to control the operation of the IPG 14 in accordance with a selected operating program and stimulation parameters (and if generated, the parameters output by the noise generation circuitry 61) stored in the memory 80. In controlling the operation of the IPG 14, the microcontroller 74 is able to individually generate stimulus pulses and electrical background energy at the electrical terminals 68 using the analog output circuitry 60, in combination with the control logic 62 and timer logic circuitry 66, thereby allowing each electrical terminal 68 (and thus, each electrode 26) to be paired or grouped with other electrical terminals 68 (and thus, other electrodes 26), including the monopolar case electrode, to control the polarity, amplitude, rate, pulse width, pulse shape, burst rate, and channel through which the current stimulus pulses and associated electrical background energy are provided. The microcontroller 74 facilitates the storage of electrical parameter data measured by the monitoring circuitry 70 within memory 80.

The IPG 14 further comprises a receiving coil 84 for receiving programming data (e.g., the operating program and/or stimulation parameters) from the external programmer (i.e., the RC 16 or CP 18) in an appropriate modulated carrier signal, and charging, and circuitry 86 for demodulating the carrier signal it receives through the receiving coil 84 to recover the programming data, which programming data is then stored within the memory 80, or within other memory elements (not shown) distributed throughout the IPG 14.

The IPG 14 further comprises back telemetry circuitry 88 and a transmission coil 90 for sending informational data to the external programmer. The back telemetry features of the IPG 14 also allow its status to be checked. For example, when the CP 18 initiates a programming session with the IPG 14, the capacity of the battery is telemetered, so that the CP 18 can calculate the estimated time to recharge. Any changes made to the current stimulus parameters are confirmed through back telemetry, thereby assuring that such changes have been correctly received and implemented within the implant system. Moreover, upon interrogation by the CP 18, all programmable settings stored within the IPG 14 may be uploaded to the CP 18.

The IPG 14 further comprises a rechargeable power source 92 and power circuits 94 for providing the operating power to the IPG 14. The rechargeable power source 92 may, e.g., comprise a lithium-ion or lithium-ion polymer battery or other form of rechargeable power. The rechargeable source 92 provides an unregulated voltage to the power circuits 94. The power circuits 94, in turn, generate the various voltages 96, some of which are regulated and some of which are not, as needed by the various circuits located within the IPG 14. The rechargeable power source 92 is recharged using rectified AC power (or DC power converted from AC power through other means, e.g., efficient AC-to-DC converter circuits) received by the receiving coil 84.

To recharge the power source 92, the external charger 22 (shown in FIG. 1), which generates the AC magnetic field, is placed against, or otherwise adjacent, to the patient's skin over the implanted IPG 14. The AC magnetic field emitted by the external charger induces AC currents in the receiving coil 84. The charging and forward telemetry circuitry 86 rectifies the AC current to produce DC current, which is used to charge the power source 92. While the receiving coil 84 is described as being used for both wirelessly receiving communications (e.g., programming and control data) and charging energy from the external device, it should be appreciated that the receiving coil 84 can be arranged as a dedicated charging coil, while another coil, such as the coil 90, can be used for bi-directional telemetry.

Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference.

It should be noted that rather than an IPG, the SCS system 10 may alternatively utilize an implantable receiver-stimulator (not shown) connected to the stimulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation energy and background energy in accordance with the control signals.

Figure 9:
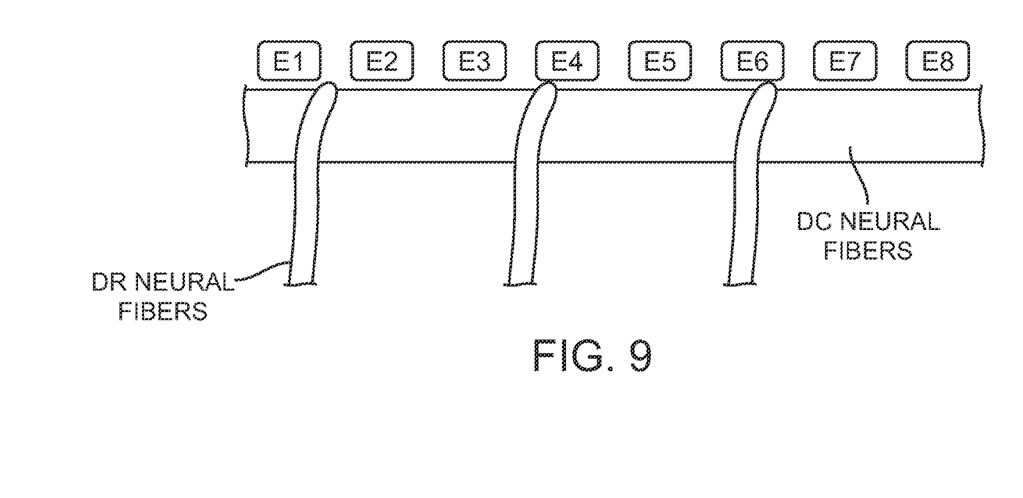
FIG. 9 is a lateral view of electrodes rostral-caudally implanted along the spinal cord.

Referring to FIG. 9, a method of using the SCS system 10 to stimulate DC neural fibers, while decreasing the excitability of DR neural fibers, will be described. As there shown, electrodes E1-E8 are rostro-caudally arranged along DC neural fibers. Electrodes E1 and E2 are configured as stimulating electrodes in a bipolar arrangement, while the electrode E1 is configured as a background electrode in a monopolar arrangement with the case. Thus, electrical stimulation energy is conveyed between electrodes E1 and E2, thereby therapeutically stimulating the DC neural fibers, e.g., to relieve pain suffered by the patient, and electrical background energy is conveyed between electrode E1 and the case, thereby modulating the excitability of the DR neural fibers. Alternatively, the electrical background energy may be conveyed from electrodes that are not used for stimulation (e.g., electrode E3). In either event, the electrical stimulation energy and the electrical background energy can be conveyed in accordance stimulation parameters that, e.g., generate the waveforms illustrated in FIGS. 4-6.

Notably, due to the monopolar arrangement, the field strength of the electrical background energy conveyed from the electrode E1 decays at a relatively low rate with distance. As such, the electrode E1 may be relatively far from the DR neural fibers for it to modulate the excitability of the DR neural fibers. Furthermore, due to the orientation and location of the DR neural fibers to the monopolar electrical field relative to the DC neural fibers, the electrical background energy will advantageously have a greater effect on the DR neural fibers than the DC neural fibers (i.e., the excitability of the DR neural fibers will be modulated more than the excitability of the DC neural fibers).

Alternatively, the electrical background energy may be conveyed from electrodes in bipolar arrangement. However, in this case, due to current shunting, the electrodes must be relatively close to the DR neural fibers. In either case, as a general rule, the excitability of the DR neural fibers will be decreased if the magnitude of the electrical background energy is relatively high, and the excitability of the DR neural fibers will be increased if the magnitude of the electrical background energy is relatively low. The optimum magnitude selected for the electrical background energy will ultimately depend on the particular stimulation application and the distance between the electrode or electrodes through which the electrical background energy is conveyed at the nerve fibers whose excitability is to be modulated.

Because the excitability of the DR neural fibers will be modulated by the electrical background energy, the effect that the inadvertent conveyance of the electrical stimulation energy to the DR neural fibers will be modified. Because it is desirable to decrease the excitability of the DR neural fibers in this case, the magnitude of the conveyed electrical background energy should be set relatively high. In one method, the electrical background energy is set equal to or higher than 10% of the perception threshold of the patient. Preferably, the electrical background energy is sub-threshold (i.e., does not stimulate nerve fibers), but may be supra-threshold if it provides therapy to the patient or can otherwise be tolerated by the patient. Ultimately, the magnitudes of the electrical stimulation energy and electrical background energy can be set relative to each other through trial and error.

In a practical implementation, the surgeon/clinician may program the IPG 14 with the CP 18 (shown in FIG. 1) to select the stimulation parameter set that recruits the DC neural fibers that interact, via the dorsal horn, with the DR neural fibers that innervate the dermatomes corresponding to the region of pain experienced by the patient. In accordance with the programmed stimulation parameters, the IPG 14 will convey the electrical stimulation energy via the selected electrodes (in this case, electrodes E1, E2) and electrical background energy via the selected electrodes (in this case, electrode E1 and the IPG case). Alternatively, the IPG 14 may be programmed to not convey electrical background energy at this point in time. If necessary, the magnitude of the electrical stimulation energy may be increased independent of the magnitude of the electrical background energy to recruit or activate more DC nerve fibers in order provide adequate therapy to the patient. If the increase the magnitude of the electrical stimulation energy over-stimulates the DR nerve fibers, the magnitude of electrical background energy may be increased relative to the magnitude of the electrical stimulation energy, or if not already turned on, may be turned on. Once the excitability of the DR nerve fibers is decreased a sufficient amount by the electrical background energy, the magnitude of the electrical stimulation energy may be increased until sufficient therapy is provided.

Thus, it can be appreciated that the conveyance of the electrical background energy to the DR nerve fibers reduces the excitability of the DR nerve fibers to an extent that prevents, or at least reduces, inadvertent stimulation of the DR nerve fibers by the conveyed electrical stimulation energy that would have otherwise occurred absent the electrical background energy. As a result, the amount of monosynaptic reflect in the dorsal horn is reduced or eliminated, thereby reducing the likelihood of uncomfortable side effects typically associated with the stimulation of DR nerve fibers.

As briefly stated above, the excitability of nerve fibers may be increased if the magnitude of the electrical background energy is relatively low. This may have applications if stimulation of a particular tissue region is to be enhanced. For example, the electrode or electrodes closest to the DC nerve fibers may be used to convey electrical background energy to the DC nerve fibers, thereby enhancing the stimulation of these DC nerve fibers via electrical stimulation energy. In this case, it may be desirable to convey the electrical background energy between electrodes in a bipolar arrangement in order to isolate the stimulation enhancing effect of the electrical background energy to the desired nerve fibers.

Whether the excitability of neural tissue is decreased or increased, it can be appreciated from the foregoing description that electrical background energy may be used to preferentially activate or recruit neural tissue targeted for stimulation over neural tissue not targeted for stimulation.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method of providing therapy to a patient, comprising:
   conveying electrical background energy in accordance with at least one stochastic parameter to a first tissue region of the patient, thereby substantially modulating the excitability of the first tissue region;
   conveying electrical stimulation energy to the first tissue region when its excitability is modulated, wherein the excitability of the first tissue region is modulated by decreasing the excitability of the first tissue region, thereby reducing any adverse effect that the conveyed electrical stimulation energy has on the first tissue region, and wherein the electrical stimulation energy is conveyed during the entirety of a time period and the electrical background energy is conveyed at least during a portion of the time period; and
   conveying the electrical stimulation energy to a second tissue region of the patient, thereby therapeutically stimulating the second tissue region.

2. The method of claim 1, wherein the decreased excitability of the first tissue region prevents stimulation of the first tissue region by the conveyed electrical stimulation energy.

3. The method of claim 1, wherein the second tissue region comprises dorsal column (DC) neural fibers, and the first tissue region comprises dorsal root (DR) neural fibers.

4. The method of claim 1, wherein the electrical background energy comprises pulses, and the at least one stochastic parameter comprises at least one of an interpulse interval, pulse amplitude, pulse shape, and pulse duration.

5. The method of claim 1, wherein the magnitude of the electrical background energy is equal to or less than one-tenth the perception threshold of the patient.

6. The method of claim 1, wherein the magnitude of the electrical background energy is greater than 2% of the magnitude of the electrical stimulation energy.

7. The method of claim 1, wherein the magnitude of the electrical background energy is greater than 10% of the magnitude of the electrical stimulation energy.

8. The method of claim 1, wherein the magnitude of the electrical background energy is less than 50% of the magnitude of the electrical stimulation energy.

9. The method of claim 1, wherein the electrical background energy is sub-threshold.

10. The method of claim 1, wherein the electrical background energy is supra-threshold.

11. The method of claim 1, wherein the electrical background energy is conveyed during the conveyance of the electrical stimulation energy.

12. The method of claim 1, wherein the electrical stimulation energy comprises a train of stimulus pulses.

13. The method of claim 12, wherein the electrical background energy is continuous and is conveyed during the train of stimulus pulses.

14. The method of claim 12, wherein the electrical background energy comprises a plurality of background pulses.

15. The method of claim 14, wherein the background pulses are respectively pre-pulses to the stimulus pulses.

16. The method of claim 1, further comprising adjusting the magnitude of the electrical background energy relative to the magnitude of the electrical stimulation energy.

17. The method of claim 1, wherein the conveyed of the electrical stimulation energy provides pain relief to the patient.

18. A neurostimulator, comprising:
   a plurality of electrical terminals configured for being electrically coupled to at least one electrode carrying stimulation lead;
   analog output circuitry configured for generating electrical stimulation energy and for generating electrical background energy in accordance with at least one stochastic parameter, wherein the electrical background energy comprises white noise, and the at least one stochastic parameter comprises a frequency; and
   control circuitry configured for controlling the analog output circuitry to convey the electrical stimulation energy to the plurality of electrical terminals during an entirety of a time period and the electrical background energy to the plurality of electrical terminals during at least a portion of the time period.

19. The neurostimulator of claim 18, wherein the electrical background energy comprises pulses, and the at least one stochastic parameter comprises at least one of an interpulse interval, pulse amplitude, pulse shape, and pulse duration.

20. The neurostimulator of claim 19, wherein the analog output circuitry comprises a white noise generator configured for generating the white noise, a bandpass filter configured for filtering the white noise, a pulse mixer configured for stochastically varying at least one parameter in accordance with the filtered white noise, and outputting the at least one stochastically varied parameter as the at least one stochastic parameter in accordance with which the electrical background energy is generated.

21. The neurostimulator of claim 18, wherein the magnitude of the electrical background energy is greater than 2% of the magnitude of the electrical stimulation energy.

22. The neurostimulator of claim 18, wherein the magnitude of the electrical background energy is greater than 10% of the magnitude of the electrical stimulation energy.

23. The neurostimulator of claim 18, wherein the magnitude of the electrical background energy is less than 50% of the magnitude of the electrical stimulation energy.

24. The neurostimulator of claim 18, wherein at least one of the electrical terminals to which the electrical background energy is the same as at least one of the electrical terminals to which the electrical stimulation energy is conveyed.

25. The neurostimulator of claim 18, wherein none of the electrical terminals to which the electrical background energy is conveyed is the same as an electrical terminal to which the electrical stimulation energy is conveyed.

26. The neurostimulator of claim 18, wherein the control circuitry is configured for controlling the analog output circuitry to convey the electrical background energy to the plurality of electrical terminals during the conveyance of the electrical stimulation energy to the plurality of electrical terminals.

27. The neurostimulator of claim 18, wherein the electrical stimulation energy comprises a train of stimulus pulses having a fixed pulse frequency.

28. The neurostimulator of claim 27, wherein the electrical background energy is continuous and is conveyed during the train of stimulus pulses.

29. The neurostimulator of claim 27, wherein the electrical background energy comprises a plurality of background pulses.

30. The neurostimulator of claim 29, wherein the background pulses are respectively pre-pulses to the stimulus pulses.

31. The neurostimulator of claim 18, wherein the control circuitry is configured for adjusting the magnitude of the electrical background energy relative to the magnitude of the electrical stimulation energy.

32. The neurostimulator of claim 18, wherein the control circuitry is configured for controlling the analog output circuitry to convey the electrical stimulation energy in a bipolar manner and to convey the electrical background energy in a monopolar manner.

33. The neurostimulator of claim 18, further comprising a case containing the plurality of electrical terminals, analog output circuitry, and control circuitry to form an implantable neurostimulator.

34. A neurostimulator, comprising:
   a plurality of electrical terminals configured for being electrically coupled to at least one electrode carrying stimulation lead;
   analog output circuitry configured for generating electrical stimulation energy and for generating electrical background energy in accordance with at least one stochastic parameter; and
   control circuitry configured for controlling the analog output circuitry to convey the electrical stimulation energy to the plurality of electrical terminals in a bipolar manner during an entirety of a time period and the electrical background energy to the plurality of electrical terminals in a monopolar manner during at least a portion of the time period.

35. The neurostimulator of claim 34, wherein the electrical background energy comprises pulses, and the at least one stochastic parameter comprises at least one of an interpulse interval, pulse amplitude, pulse shape, and pulse duration.

36. The neurostimulator of claim 34, wherein the magnitude of the electrical background energy is greater than 2% of the magnitude of the electrical stimulation energy.

37. The neurostimulator of claim 34, wherein the magnitude of the electrical background energy is greater than 10% of the magnitude of the electrical stimulation energy.

38. The neurostimulator of claim 34, wherein the magnitude of the electrical background energy is less than 50% of the magnitude of the electrical stimulation energy.

39. The neurostimulator of claim 34, wherein at least one of the electrical terminals to which the electrical background energy is the same as at least one of the electrical terminals to which the electrical stimulation energy is conveyed.

40. The neurostimulator of claim 34, wherein none of the electrical terminals to which the electrical background energy is conveyed is the same as an electrical terminal to which the electrical stimulation energy is conveyed.

41. The neurostimulator of claim 34, wherein the control circuitry is configured for controlling the analog output circuitry to convey the electrical background energy to the plurality of electrical terminals during the conveyance of the electrical stimulation energy to the plurality of electrical terminals.

42. The neurostimulator of claim 34, wherein the electrical stimulation energy comprises a train of stimulus pulses having a fixed pulse frequency.

43. The neurostimulator of claim 42, wherein the electrical background energy is continuous and is conveyed during the train of stimulus pulses.

44. The neurostimulator of claim 42, wherein the electrical background energy comprises a plurality of background pulses.

45. The neurostimulator of claim 44, wherein the background pulses are respectively pre-pulses to the stimulus pulses.

46. The neurostimulator of claim 34, wherein the control circuitry is configured for adjusting the magnitude of the electrical background energy relative to the magnitude of the electrical stimulation energy.

47. The neurostimulator of claim 34, wherein the control circuitry is configured for controlling the analog output circuitry to convey the electrical stimulation energy in a bipolar manner and to convey the electrical background energy in a monopolar manner.

48. The neurostimulator of claim 34, further comprising a case containing the plurality of electrical terminals, analog output circuitry, and control circuitry to form an implantable neurostimulator.

* * * * *